United States Patent
Kamo et al.

(10) Patent No.: US 10,884,223 B2
(45) Date of Patent: Jan. 5, 2021

(54) OBJECTIVE OPTICAL SYSTEM FOR ENDOSCOPE

(71) Applicant: OLYMPUS CORPORATION, Hachioji (JP)

(72) Inventors: Yuji Kamo, Hino (JP); Yoshifumi Tsuji, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 197 days.

(21) Appl. No.: 16/193,766

(22) Filed: Nov. 16, 2018

(65) Prior Publication Data

US 2019/0086647 A1    Mar. 21, 2019

Related U.S. Application Data

(63) Continuation of application No. PCT/JP2017/017747, filed on May 10, 2017.

(30) Foreign Application Priority Data

Jun. 15, 2016  (JP) .................................. 2016-119152

(51) Int. Cl.
*G02B 23/24* (2006.01)
*G02B 13/04* (2006.01)
*A61B 1/00* (2006.01)

(52) U.S. Cl.
CPC ............ *G02B 13/04* (2013.01); *A61B 1/0011* (2013.01); *A61B 1/00096* (2013.01);
(Continued)

(58) Field of Classification Search
CPC ........ G02B 13/04; G02B 23/243; G02B 9/00;
G02B 9/60; G02B 9/34; G02B 13/18; G02B 21/00; G02B 21/0032; G02B 21/0052; G02B 21/24; A61B 1/00096; A61B 1/0011; A61B 1/00188; A61B 1/00197;
(Continued)

(56) References Cited

U.S. PATENT DOCUMENTS

| 4,037,938 A | 7/1977 | Yamashita et al. |
| 5,198,931 A | 3/1993 | Igarashi |

(Continued)

FOREIGN PATENT DOCUMENTS

| JP | 51062053 A | 5/1976 |
| JP | H107181377 A | 7/1995 |

(Continued)

OTHER PUBLICATIONS

International Search Report (ISR) dated Aug. 1, 2017 issued in International Application No. PCT/JP2017/017747.
(Continued)

*Primary Examiner* — Arnel C Lavarias
(74) *Attorney, Agent, or Firm* — Holtz, Holtz & Volek PC

(57) ABSTRACT

An objective optical system for an endoscope includes, in order from an object side, a first lens having a negative refractive power, a second meniscus lens having a positive refractive power and having a convex surface directed toward an image side, an aperture stop, a third lens having a positive refractive power, and a cemented lens of a fourth lens having a positive refractive power and a fifth lens having a negative refractive power.

10 Claims, 4 Drawing Sheets

(52) U.S. Cl.
CPC ...... *A61B 1/00188* (2013.01); *A61B 1/00197* (2013.01); *G02B 23/243* (2013.01); *A61B 1/00186* (2013.01)

(58) Field of Classification Search
CPC ............ A61B 1/00186; A61B 1/00002; A61B 1/00064; A61B 1/04; A61B 1/06
USPC ....... 359/434, 362, 363, 368, 369, 754, 763, 359/770; 600/101, 109, 130, 160, 162, 600/163, 167, 176, 181
See application file for complete search history.

(56) References Cited

U.S. PATENT DOCUMENTS

| | | | | |
|---|---|---|---|---|
| 5,777,797 | A * | 7/1998 | Miyano | G02B 23/243 359/660 |
| 6,956,703 | B2 * | 10/2005 | Saito | G02B 9/34 359/660 |
| 8,477,436 | B2 * | 7/2013 | Sasamoto | A61B 1/00188 359/793 |
| 9,568,725 | B2 * | 2/2017 | Ushio | G02B 27/0081 |
| 10,007,105 | B2 * | 6/2018 | Kamo | G02B 9/60 |
| 10,018,827 | B2 * | 7/2018 | Ushio | G02B 9/34 |
| 2008/0055741 | A1 | 3/2008 | Asami | |
| 2012/0113533 | A1 | 5/2012 | Kubota et al. | |
| 2012/0127598 | A1 | 5/2012 | Katahira | |
| 2012/0147164 | A1 | 6/2012 | Sasamoto | |
| 2012/0224268 | A1 | 9/2012 | Takato | |
| 2016/0306162 | A1 | 10/2016 | Ushio | |

FOREIGN PATENT DOCUMENTS

| | | |
|---|---|---|
| JP | 2009075141 A | 4/2009 |
| JP | 2009109576 A | 5/2009 |
| JP | 2012103319 A | 5/2012 |
| JP | 4997348 B2 | 8/2012 |
| JP | 2012230434 A | 11/2012 |
| JP | 5927368 B1 | 6/2016 |
| WO | 2011145505 A1 | 11/2011 |
| WO | 2012008312 A1 | 1/2012 |
| WO | 2016031586 A1 | 3/2016 |

OTHER PUBLICATIONS

Written Opinion dated Aug. 1, 2017 issued in International Application No. PCT/JP2017/017747.
Japanese Office Action dated Dec. 6, 2017 issued in counterpart Japanese Patent Application No. 2017-558766.
Iternational Preliminary Report on Patentabilirty (IPRP) (and English language translation thereof) and Written Opinion dated Dec. 18, 2018 issued in counterpart International Application No. PCT/JP2017/017747.
Chinese Office Action (and English language translation thereof) dated Aug. 3, 2020, issued in counterpart Chinese Application No. 201780026859.1.

* cited by examiner

OBJECTIVE OPTICAL SYSTEM FOR ENDOSCOPE

CROSS-REFERENCE TO RELATED APPLICATION

The present application is a continuation application of PCT/JP2017/017747 filed on May 10, 2017 which is based upon and claims the benefit of priority from Japanese Patent Application No. 2016-119152 filed on Jun. 15, 2016; the entire contents of which are incorporated herein by reference.

BACKGROUND OF THE INVENTION

Field of the Invention

The present invention relates to an objective optical system for endoscope, and particularly to an objective optical system for endoscope that is used in a medical field and an industrial field.

Description of the Related Art

Endoscope is an apparatus that has been widely used in the medical field and the industrial field. Particularly, in the medical field, endoscopes have been used for diagnosis and treatment of parts observed, from images achieved by an endoscope inserted inside the body cavity.

An optical system of endoscope provides focused images from a near-point object up to a far-point object by setting an appropriate Fno (F-number) and a focusing position. Moreover, a lens diameter and an overall optical length are made small. Accordingly, an endoscope which is thin, and which does not cause pain to a subject at the time of insertion into the body cavity, and furthermore has an ability to turn in a small radius inside the body, is arranged. Moreover, in recent years, endoscopes with further improved image quality and small size have been sought.

Small-size objective optical systems for endoscope have been proposed in the following patent literatures.

An endoscope objective lens unit proposed in Japanese Patent No. 4997348 Publication, has a relatively fast F-number of about 4, and an optical performance is such that correction of a longitudinal chromatic aberration and an astigmatism is inadequate for large number of pixels, and there are limitations to realize the high performance.

Moreover, an objective optical system proposed in International Unexamined Patent Application Publication No. 2012/008312 has an Fno of about 5.5 and is an optical system which is not suitable for a small pixel pitch.

Moreover, an image pickup lens proposed in Japanese Patent Application Laid-open Publication No. 2009-75141 has an Fno of about 2, and is a bright optical system. However, the bright optical system is for improvement of the fast Fno, and a problem of a manufacturing error with respect to a small pixel pitch has not been taken into consideration. Moreover, the image pickup lens that has been disclosed is for mounting on a car, and the small-sizing necessary for use in an endoscope has not been accomplished.

Moreover, an endoscope objective lens proposed in Japanese Patent Application Laid-open Publication No. Sho 51-62053 has a small size, and has an optical system having a relatively fast Fno. However, examples that have been disclosed are for fiber, and an effect of a manufacturing error due to small pixel pitch has not been taken into consideration in design.

Moreover, an endoscope objective optical system proposed in Japanese Patent No. 5927368 Publication is an optical system having a fast Fno suitable for a small pixel pitch, and a manufacturing error of focus has also been taken into consideration. However, one surface being formed of a flat surface field lens, there are some limitations on an effect that can be achieved by relaxing the manufacturing error.

Moreover, optical systems proposed Japanese Patent Application Laid-open Publication No. 2012-230434, Japanese Patent Application Laid-open Publication No. Hei 7-181377, and Japanese Patent Application Laid-open Publication No. 2012-103319, a point of small-sizing and a point related to an error sensitivity of focusing have not been taken into consideration.

SUMMARY OF THE INVENTION

An objective optical system according to at least some embodiments of the present invention consists of in order from an object side, a first lens having a negative refractive power, a second meniscus lens having a positive refractive power and having a convex surface directed toward an image side, an aperture stop, a third lens having a positive refractive power, and a cemented lens of a fourth lens having a positive refractive power and a fifth lens having a negative refractive power, wherein the objective optical system satisfies the following conditional expressions (1-1), (1-2), and (1-3).

$$-0.6 \leq f1/f45 \leq -0.18 \tag{1-1}$$

$$0.2 \leq (r3f+r3r)/(r3f-r3r) \leq 1 \tag{1-2}$$

$$0.15 \leq d34/d4 \leq 0.7 \tag{1-3}$$

where, f1 denotes a focal length of the first lens, f45 denotes a combined focal length of the fourth lens and the fifth lens, r3f denotes a radius of curvature of an object side of the third lens, r3r denotes a radius of curvature of an image side of the third lens, d34 denotes a distance along an optical axis between the third lens and the fourth lens, and d4 denotes a thickness of the fourth lens.

DETAILED DESCRIPTION OF THE INVENTION

An objective optical system for endoscope according to an embodiment will be described below in detail by referring to the accompanying diagrams. However, the present invention is not restricted to the embodiment described below.

Figure 1:
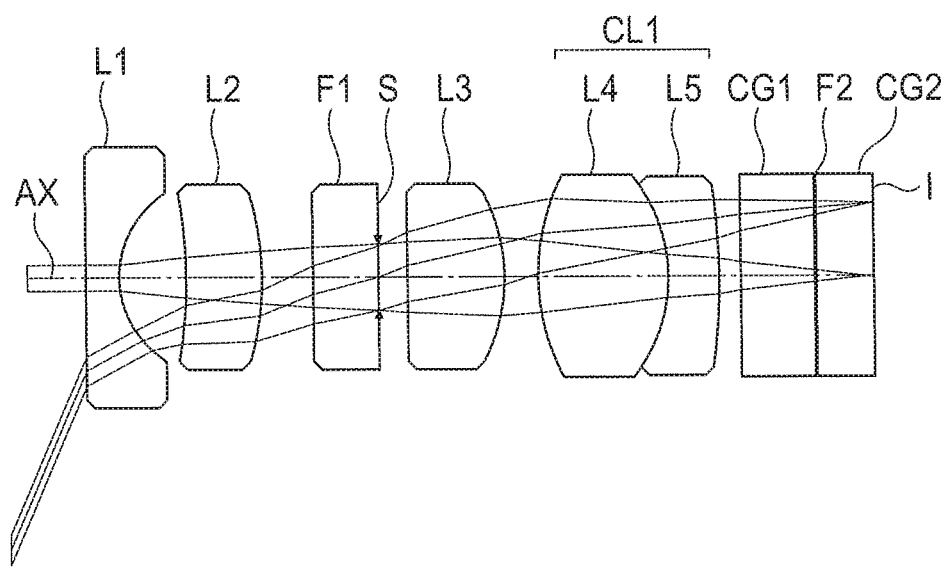
FIG. 1 is a diagram showing a cross-sectional view of a lens arrangement of an objective optical system for endoscope according to an embodiment of the present invention.

FIG. 1 is a lens cross-sectional view of the objective optical system for endoscope according to the present embodiment.

The objective optical system for endoscope according to the present embodiment includes in order from an object side, a first lens L1 having a negative refractive power, a second meniscus lens L2 having a positive refractive power and having a convex surface directed toward an image side, an infrared absorbing filter F1, an aperture stop S, a third lens L3 having a positive refractive power, and a cemented lens CL1 of a fourth lens L4 having a positive refractive power and a fifth lens L5 having a negative refractive power, wherein the objective optical system for endoscope satisfies the following conditional expressions (1-1), (1-2), and (1-3).

$$-0.6 \leq f1/f45 \leq -0.18 \quad (1\text{-}1)$$

$$0.2 \leq (r3f+r3r)/(r3f-r3r) \leq 1 \quad (1\text{-}2)$$

$$0.15 \leq d34/d4 \leq 0.7 \quad (1\text{-}3)$$

where, f1 denotes a focal length of the first lens L1, f45 denotes a combined focal length of the fourth lens L4 and the fifth lens L5, r3f denotes a radius of curvature of an object side of the third lens L3, r3r denotes a radius of curvature of an image side of the third lens L3, d34 denotes a distance along an optical axis between the third lens L3 and the fourth lens L4, and d4 denotes a thickness of the fourth lens L4.

Reasons for and effects of adopting such arrangement in the present embodiment will be described below. In an endoscope, generally it is necessary to observe an area over a wide range, and a lens front-cell diameter has to be made small. Therefore, in the present embodiment, a retro-focus arrangement is adopted.

Therefore, the first lens L1 having a negative refractive power is disposed nearest to object, and a negative refractive power necessary for the retro-focus arrangement is secured. Moreover, the second meniscus lens L2 having a positive refractive power and having the convex surface directed toward the image side is disposed on the image side of the first lens L1 to correct an aberration that occurs in the first lens L1 having a negative refractive power.

Furthermore, by disposing on the image side of the second meniscus lens L2 having a positive refractive power, in order from the object side, the aperture stop S, the third lens L3 which is a biconvex positive lens having a positive refractive power and which contributes mainly to image formation, and the cemented lens CL1 in which the fourth lens L4 which is a biconvex positive lens and the fifth lens L5 having a negative refractive power are cemented, at positions where a marginal-ray height becomes high, a chromatic aberration is corrected. The cemented lens CL1 is arranged to have a positive refractive power as a whole in order to contribute to image formation together with the third lens L3 having a positive refractive power.

Moreover, as a pixel pitch becomes small due to the number of pixels becoming large, a diameter of a permissible circle of confusion becomes small. Accordingly, a high accuracy, and particularly an accuracy of focusing position is sought. For this, in the present embodiment, the positive refractive power of the cemented lens CL1 of the fifth lens L5 and the fourth lens L4 near the image plane is made relatively strong. As a result, an arrangement is made such that an optical longitudinal magnification when moved together with an image sensor becomes small, and it is possible to reduce an error sensitivity of focusing.

At this time, the first lens L1 is required to have a relatively strong negative refractive power for shortening the overall length while making an arrangement of the retro-focus type. Therefore, it is necessary to correct in the fourth lens L4 and the fifth lens L5, an aberration which occurs, while taking into consideration the error sensitivity of focusing. For this, it is desirable to satisfy the following conditional expression.

$$-0.6 \leq f1/f45 \leq -0.18 \quad (1\text{-}1)$$

where, f1 denotes the focal length of the first lens L1, f45 denotes the combined focal length of the fourth lens L4 and the fifth lens L5.

Conditional expression (1-1) is related to an appropriate ratio of f1 and f45. When an upper limit value of conditional expression (1-1) is exceeded, an amount of aberration occurring in the first lens L1 becomes large and either a coma is deteriorated or the error sensitivity of focusing becomes strong.

When a value falls below a lower limit value of conditional expression (1-1), the overall length of the optical system becomes long. An amount of aberration occurring in the fourth lens L4 and the fifth lens L5 becomes large, and an astigmatism, the coma, and a chromatic aberration of magnification are deteriorated.

Moreover, at this time, since the positive refractive power of the fourth lens L4 becomes strong, it is necessary to control an amount of aberration that occurs in the third lens L3 having a positive refractive power, which is involved in image formation. Therefore, it is desirable that the third lens L3 satisfies the following conditional expression (1-2).

$$0.2 \leq (r3f+r3r)/(r3f-r3r) \leq 1 \quad (1\text{-}2)$$

where, r3f denotes a radius of curvature of an object side of the third lens L3, and r3r denotes a radius of curvature of an image side of the third lens L3.

Conditional expression (1-2) is related to an appropriate ratio of (r3f+r3r) and (r3f−r3r). When an upper limit value of conditional expression (1-2) is exceeded, the third lens L3 becomes meniscus-shaped. As a result, it becomes difficult to suppress an aberration that occurs in the fourth lens L4, and a spherical aberration and the coma are deteriorated.

When a value falls below a lower limit value of conditional expression (1-2), either a principal point moves toward the object side and the overall length becomes long, or an amount of the spherical aberration in the third lens L3 becomes large and the performance is degraded.

Moreover, at this time, since the positive refractive power of the fourth lens L4 becomes strong, a manufacturing error of the cemented lens of the fourth lens L4 and the fifth lens L5, and particularly, a degradation of performance due to decentering of lenses such as shifting and tilting, becomes large. Therefore, it is desirable to make an arrangement such that an angle of incidence on the image sensor is narrowed with respect to the optical axis AX to be closer to telecentric, or in other words, an arrangement is made such that light is incident substantially perpendicularly on an image pickup surface of the image sensor, as this leads to less degradation of performance. For this, it is desirable to satisfy the following conditional expression (1-3) in order to keep a distance from the aperture stop S with respect to the fourth lens L4 as long as possible.

$$0.15 \leq d34/d4 \leq 0.7 \quad (1\text{-}3)$$

where, d34 denotes a distance along an optical axis AX between the third lens L3 and the fourth lens L4, and d4 denotes a thickness of the fourth lens L4.

Conditional expression (1-3) is related to an appropriate ratio of d34 and d4. When an upper limit value of conditional expression (1-3) is exceeded, either the overall length of the optical system becomes long or a light-ray height at the fourth lens L4 becomes high and a lens diameter becomes large.

When a value falls below a lower limit value of conditional expression (1-3), a distance between the fourth lens L4 and the aperture stop S becomes excessively small, and an angle of incidence is widened with respect to the optical axis AX, or in other words, an angle of incidence on a lens surface becomes large. Consequently, the performance is susceptible to be degraded with respect to a manufacturing error of the fourth lens L4.

It is more desirable to satisfy the following conditional expression (1-1)' instead of conditional expression (1-1).

$$-0.5 \leq f1/f45 \leq -0.22 \quad (1\text{-}1)'$$

Moreover, it is even more desirable to satisfy the following conditional expression (1-1)" instead of conditional expression (1-1).

$$-0.4 \leq f1/f45 \leq -0.24 \quad (1\text{-}1)''$$

It is more desirable to satisfy the following conditional expression (1-2)' instead of conditional expression (1-2).

$$0.4 \leq (r3f+r3r)/(r3f-r3r) \leq 1 \quad (1\text{-}2)'$$

Moreover, it is even more desirable to satisfy the following conditional expression (1-2)" instead of conditional expression (1-2).

$$0.6 \leq (r3f+r3r)/(r3f-r3r) \leq 1 \quad (1\text{-}2)''$$

It is more desirable to satisfy the following conditional expression (1-3)' instead of conditional expression (1-3).

$$0.18 \leq d34/d4 \leq 0.6 \quad (1\text{-}3)'$$

Moreover, it is even more desirable to satisfy the following conditional expression (1-3)" instead of conditional expression (1-3).

$$0.2 \leq d34/d4 \leq 0.5 \quad (1\text{-}3)''$$

When a balance of the third lens L3 and the fourth lens L4 is changed while maintaining the overall positive refractive power, an aberration is susceptible to be deteriorated. Therefore, it is preferable to set the respective radii of curvature appropriately.

In other words, according to a preferable aspect of the present embodiment, it is desirable that the radius of curvature of the image side of the third lens L3 and a radius of curvature of an image side of the fourth lens L4 satisfy the following conditional expression (2).

$$0.7 \leq r4r/r3r \leq 1.2 \quad (2)$$

where, r4r denotes the radius of curvature of the image side of the fourth lens L4, and r3r denotes the radius of curvature of the image side of the third lens L3.

Conditional expression (2) is related to an appropriate ratio of r4r and r3r. When an upper limit value of conditional expression (2) is exceeded, either the radius of curvature of the image side of the third lens L3 becomes large, and the overall length becomes long, or the radius of curvature of the image side of the fourth lens L4 becomes small, and correction of the coma and the chromatic aberration of magnification becomes excessive.

When a value falls below a lower limit value of conditional expression (2), either the radius of curvature of the image side of the third lens L3 becomes small and the spherical aberration is deteriorated, or the radius of curvature of the image side of the fourth lens L4 becomes large and correction of the coma and the chromatic aberration of magnification becomes inadequate.

It is more desirable to satisfy the following conditional expression (2)' instead of conditional expression (2).

$$0.73 \leq r4r/r3r \leq 1.1 \quad (2)'$$

Moreover, it is even more desirable to satisfy the following conditional expression (2)" instead of conditional expression (2).

$$0.75 \leq r4r/r3r \leq 1 \quad (2)''$$

Moreover, the fourth lens L4 and the fifth lens L5 in the cemented lens CL1 have to suppress an aberration in a peripheral portion of image field that occurs in the first lens L1 while maintaining a relatively strong positive refractive power.

Therefore, according to a preferable aspect of the present embodiment, it is desirable that a radius of curvature of an object side of the fourth lens L4 and a radius of curvature of an image side of the fifth lens L5 satisfy the following conditional expression (3).

$$-0.5 \leq r4f/r5r \leq -0.05 \quad (3)$$

where, r4f denotes the radius of curvature of the object side of the fourth lens L4, and r5r denotes the radius of curvature of the image side of the fifth lens L5.

Conditional expression (3) is related to an appropriate ratio of r4f and r5r. When an upper limit value of conditional expression (3) is exceeded, either the radius of curvature of the object side of the fourth lens L4 becomes excessively small and the spherical aberration and the coma are deteriorated, or the radius of curvature of the image side of the fifth lens L5 becomes excessively large and correction of the coma and the astigmatism becomes inadequate.

When a value falls below a lower limit value of conditional expression (3), the radius of curvature of the object side of the fourth lens L4 becomes excessively large and the refractive power cannot be maintained and the overall length becomes long. Or, the radius of curvature of the image side of the fifth lens L5 becomes excessively small and correction of the coma and the astigmatism becomes excessive. Or, a radius of curvature of a cemented surface becomes small and processing of lens becomes difficult.

It is more desirable to satisfy the following conditional expression (3)' instead of conditional expression (3).

$$-0.45 \leq r4f/r5r \leq -0.1 \quad (3)'$$

Moreover, it is even more desirable to satisfy the following conditional expression (3)" instead of conditional expression (3).

$$-0.4 \leq r4f/r5r \leq -0.15 \quad (3)''$$

Moreover, when the retro-focus type is adopted, the overall length of the optical system tends to become long. Therefore, an arrangement of the third lens L3 and the fourth lens L4 having a positive refractive power becomes significant.

Therefore, according a preferable aspect of the present embodiment, it is desirable that the radius of curvature of the object side of the third lens L3 and the radius of curvature of the object side of the fourth lens L4 satisfy the following conditional expression (4).

$$0 \leq r4f/r3f \leq 0.25 \quad (4)$$

where,
r3f denotes the radius of curvature of the object side of the third lens L3, and
r4f denotes a radius of curvature of an object side of the fourth lens L4.

Conditional expression (4) is related to an appropriate ratio of r4f and r3f. When an upper limit value of conditional expression (4) is exceeded, either the radius of curvature of the object side of the third lens L3 becomes excessively small and a principal point is moved toward the object side and the overall length becomes long, or the radius of curvature of the object side of the fourth lens L4 becomes excessively large and correction of the astigmatism and the coma is inadequate.

When a value falls below a lower limit value of conditional expression (4), either the object side of the third lens L3 becomes a concave surface and as a result, the radius of curvature of the image side becomes small and the spherical aberration and the coma are deteriorated, or the object side of the fourth lens L4 becomes a concave surface and as a result, the radius of curvature of the image side becomes small, and a longitudinal chromatic aberration and the chromatic aberration of magnification are deteriorated, and the positive refractive power becomes weak and the overall length of the optical system becomes long.

It is more desirable to satisfy the following conditional expression (4)' instead of conditional expression (4).

$$0 \leq r4f/r3f \leq 0.23 \quad (4)'$$

Moreover, for realizing small-sizing and an effect of relaxing the focusing error sensitivity by the fourth lens L4 and the fifth lens L5, it is necessary to set appropriately the positive refractive power of the third lens L3.

Therefore, according to a preferable aspect of the present embodiment, it is desirable to satisfy the following conditional expression (5).

$$0.24 \leq Ih/f3 \leq 0.35 \quad (5)$$

where,
Ih denotes the maximum image height of the objective optical system for endoscope, and
f3 denotes a focal length of the third lens L3.

Conditional expression (5) is related to an appropriate ratio of IH and f3. When an upper limit value of conditional expression (5) is exceeded, either the refractive power of the third lens L3 becomes excessively strong, and an effect of lowering the focusing error sensitivity of the fourth lens L4 and the fifth lens L5 is weakened, or the spherical aberration and the coma occurring in the third lens L3 becomes large and the performance is degraded.

When a value falls below a lower limit value of conditional expression (5), the refractive power of the third lens L3 becomes excessively weak and the coma and the astigmatism occurring in the fourth lens L4 and the fifth lens L5 become large and the performance is degraded.

It is more desirable to satisfy the following conditional expression (5)' instead of conditional expression (5).

$$0.25 \leq Ih/f3 \leq 0.32 \quad (5)'$$

Moreover, when the image side of the aperture stop S, includes in order from the object side, only the third lens L3 having a positive refractive power, and the cemented lens CL1 of the fourth lens L4 having a positive refractive power and the fifth lens L5 having a negative refractive power, if a position of the aperture stop S is not set appropriately, it is not possible to fulfil the small-sizing and the focusing error sensitivity simultaneously. Therefore, it is desirable to satisfy the following conditional expression (6).

Therefore, according to a preferable aspect of the present embodiment, it is desirable that the image side of the aperture stop S consists of in order from the image side, the third lens L3 having a positive refractive power, and the cemented lens CL1 of the fourth lens having a positive refractive power and the fifth lens L5 having a negative refractive power, and the objective optical system for endoscope satisfies the following conditional expression (6).

$$0.5 \leq d1s/dsi \leq 0.8 \quad (6)$$

where,
d1s denotes a distance along the optical axis AX from the first lens L1 up to the aperture stop S, and
dsi denotes a distance along the optical axis AX from the aperture stop S up to an image plane.

Conditional expression (6) is related to an appropriate ratio of d1s and dsi. When an upper limit value of conditional expression (6) is exceeded, either an outer diameter of the first lens L1 becomes large and the small-sizing cannot be fulfilled, or the angle of incidence on the image sensor is widened with respect to the optical axis AX, and degradation of performance due to decentering of lenses such as shifting and tilting of the fourth lens L4 and the fifth lens L5 with respect to the optical axis AX, becomes large.

When a value falls below a lower limit value of conditional expression (6), the overall length of the optical system becomes long, and the refractive power of the first lens L1 becomes excessively strong, and an amount of aberrations that occurs becomes large, thereby causing degradation of performance.

It is more desirable to satisfy the following conditional expression (6)' instead of conditional expression (6).

$$0.55 \leq d1s/dsi \leq 0.7 \quad (6)'$$

Moreover, the large aberration that occurs in the first lens L1 is required to be corrected favorably in the second meniscus lens L2 and the third lens L3.

Therefore, according to a preferable aspect of the present embodiment, it is desirable to satisfy the following conditional expressions (7-1) and (7-2) simultaneously.

$$2.3 \leq f23/f \leq 4 \quad (7\text{-}1)$$

$$-0.4 \leq r1r/r2f \leq -0.1 \quad (7\text{-}2)$$

where, f23 denotes a combined focal length of the second meniscus lens L2 and the third lens L3, f denotes a focal length of the overall objective optical system for endoscope, r1r denotes a radius of curvature of an image side of the first lens L1, and r2f denotes a radius of curvature of an object side of the second meniscus lens L2.

Conditional expression (7-1) is related to an appropriate ratio of f23 and f. Conditional expression (7-2) is related to an appropriate ratio of r1r and r2f.

When an upper limit value of conditional expression (7-1) is exceeded, the positive refractive power of the second meniscus lens L2 and the third lens L3 becomes excessively weak, and it is not possible to correct the coma and the astigmatism that occur in the first lens L1.

When a value falls below a lower limit value of conditional expression (7-1), the positive refractive power of the second meniscus lens L2 and the third lens L3 become excessively strong, and the spherical aberration is deteriorated.

When an upper limit value of conditional expression (7-2) is exceeded, either the radius of curvature of the first lens L1 becomes excessively small or the radius of curvature of the second meniscus lens L2 becomes excessively large, and the coma and the astigmatism are deteriorated.

When a value falls below a lower limit value of conditional expression (7-2), either the radius of curvature of the first lens L1 becomes excessively large and the overall length becomes excessively long, or the radius of curvature of the second meniscus lens L2 becomes excessively small, and correction of the coma becomes excessive, and workability of the lens is degraded.

It is more desirable to satisfy the following conditional expression (7-1)' instead of conditional expression (7-1).

$$2.5 \leq f23/f \leq 3.5 \quad (7\text{-}1)'$$

Moreover, it is more desirable to satisfy the following conditional expression (7-2)' instead of conditional expression (7-2).

$$-0.35 \leq r1r/r2f \leq -0.12 \quad (7\text{-}2)'$$

Moreover, for fulfilling the focusing error sensitivity, the aberration in the peripheral portion of image field, and the overall length, it is necessary to take a balance of refractive index of lenses disposed on the image side of the aperture stop S.

Therefore, according to a preferable aspect of the present embodiment, it is desirable to satisfy the following conditional expressions (8-1) and (8-2).

$$0.32 \leq f3/f45 \leq 1 \quad (8\text{-}1)$$

$$-1 \leq f4/f5 \leq -0.66 \quad (8\text{-}2)$$

where, f3 denotes a focal length of the third lens L3, f45 denotes the combined focal length of the fourth lens L4 and the fifth lens L5, f4 denotes a focal length of the fourth lens L4, and f5 denotes a focal length of the fifth lens L5.

Conditional expression (8-1) is related to an appropriate ratio of f3 and f45. Conditional expression (8-2) is related to an appropriate ratio of f4 and f5.

When an upper limit value of conditional expression (8-1) is exceeded, either the refractive power of the third lens L3 becomes excessively weak and the overall length of the optical system becomes long, and correction of the spherical aberration becomes inadequate, or the refractive power of the fourth lens L4 and the fifth lens L5 becomes excessively strong and there is a degradation of performance due to decentering of lenses.

When a value falls below a lower limit value of conditional expression (8-1), either the refractive power of the third lens L3 becomes excessively strong and the spherical aberration and the coma are deteriorated, or the refractive power of the fourth lens L4 and the fifth lens L5 becomes excessively weak and an effect of lowering the focusing sensitivity is weakened.

When an upper limit value of conditional expression (8-2) is exceeded, either the refractive power of the fourth lens L4 becomes excessively strong and the coma and the astigmatism are deteriorated, or the refractive power of the fifth lens L5 becomes excessively weak and correction of the chromatic aberration of magnification becomes inadequate.

When a value falls below a lower limit value of conditional expression (8-2), either the refractive power of the fourth lens L4 becomes excessively weak and the effect of lowering the focusing sensitivity is weakened, or the refractive power of the fifth lens L5 becomes excessively strong and correction of the chromatic aberration of magnification becomes excessive and the coma is deteriorated.

It is more desirable to satisfy the following conditional expression (8-1)' instead of conditional expression (8-1).

$$0.4 \leq f3/f45 \leq 0.9 \quad (8\text{-}1)'$$

Moreover, it is more desirable to satisfy the following conditional expression (8-2)' instead of conditional expression (8-2).

$$-0.9 \leq f4/f5 \leq -0.7 \quad (8\text{-}2)$$

Moreover, for correcting favorably the aberration in the peripheral portion of the image field, it is necessary to take a balance of lenses sandwiching the aperture stop S.

Therefore, according to a preferable aspect of the present embodiment, it is desirable to satisfy the following conditional expressions (9-1) and (9-2).

$$-6.5 \leq f2/r4r \leq -3.3 \quad (9\text{-}1)$$

$$3 \leq (r2f+r2r)/(r2f-r2r) \leq 10 \quad (9\text{-}2)$$

where, f2 denotes a focal length of the second meniscus lens L2, r4r denotes a radius of curvature of an image side of the fourth lens L4, r2f denotes a radius of curvature of an object side of the second meniscus lens L2, and r2r denotes a radius of curvature of an image side of the second meniscus lens L2.

Conditional expression (9-1) is related to an appropriate ratio of f2 and r4r. Conditional expression (9-2) is related to an appropriate ratio of (r2f+r2r) and (r2f−r2r).

When an upper limit value of conditional expression (9-1) is exceeded, either the refractive power of the second meniscus lens L2 becomes excessively strong and the coma and the astigmatism are deteriorated, or the radius of curvature of the fourth lens L4 becomes excessively large and a balance of the coma and the astigmatism cannot be maintained, and is deteriorated.

When a value falls below a lower limit value of conditional expression (9-1), either the refractive power of the second meniscus lens L2 becomes excessively weak and the balance of the coma and the astigmatism cannot be maintained, and is deteriorated, or the radius of curvature of the fourth lens L4 becomes excessively small, and the spherical aberration and the coma are deteriorated.

When an upper limit value of conditional expression (9-2) is exceeded, the radius of curvature of the second meniscus lens L2 becomes excessively small, and there is an excessive correction of the spherical aberration and the coma.

When a value falls below a lower limit value of conditional expression (9-2), the radius of curvature of the second meniscus lens L2 becomes excessively large, and correction of the spherical aberration and the coma becomes inadequate.

Moreover, according to a preferable aspect of the present embodiment, it is desirable to carry out focus adjustment at the time of assembling by changing a distance between the third lens L3 and the fourth lens L4.

At the time of assembling an endoscope, the focusing position is shifted from the designed focusing position due to Newton's error and thickness error. Therefore, the positioning is to be carried out by making the focusing adjustment. It is preferable to carry out the focusing adjustment between the third lens L3 and the fourth lens L4. Accordingly, since an amount of change in focusing decreases with respect to an amount of movement in the adjustment, the adjustment becomes easy at the time of assembling, and it is possible to minimize an amount of degradation of performance due to a shift caused by hardening of an adhesive. Moreover, by shifting the fourth lens L4 and the fifth lens L5 in a direction perpendicular to the optical axis AX, a difference in left and right of an angle of view, a shift in a focusing position of the peripheral portion of the image field, and an asymmetric astigmatism may be corrected.

Moreover, when the lens arrangement is let to be a five-lens arrangement including in order from the object side, a first lens L1 having a negative refractive power, a second meniscus lens L2 having a positive refractive power and having a convex surface directed toward the image side, an aperture stop S, a third lens L3 having a positive refractive power, and a cemented lens CL1 of a fourth lens L4 having a positive refractive power and a fifth lens L5 having a negative refractive power, it is possible to shorten the overall length and to reduce the lens cost.

Moreover, it is preferable to let the first lens L1 to have the following arrangement. In an endoscope, when a dirt or blood etc. is adhered to during observation, cleaning is carried out by water jetted from a nozzle provided at a front end of the endoscope. At this time, when the lens surface is convex, the direct is hard to be cleaned, and when the lens surface is concave, water is accumulated therein. Moreover, particularly, when the lens surface is convex, the lens is susceptible to be scratched or cracked due to an impact. Therefore, it is preferable that the shape of the first lens L1 is a planoconcave shape having a flat surface directed toward the object side.

Examples will be described below.

Example 1

Figure 2A:
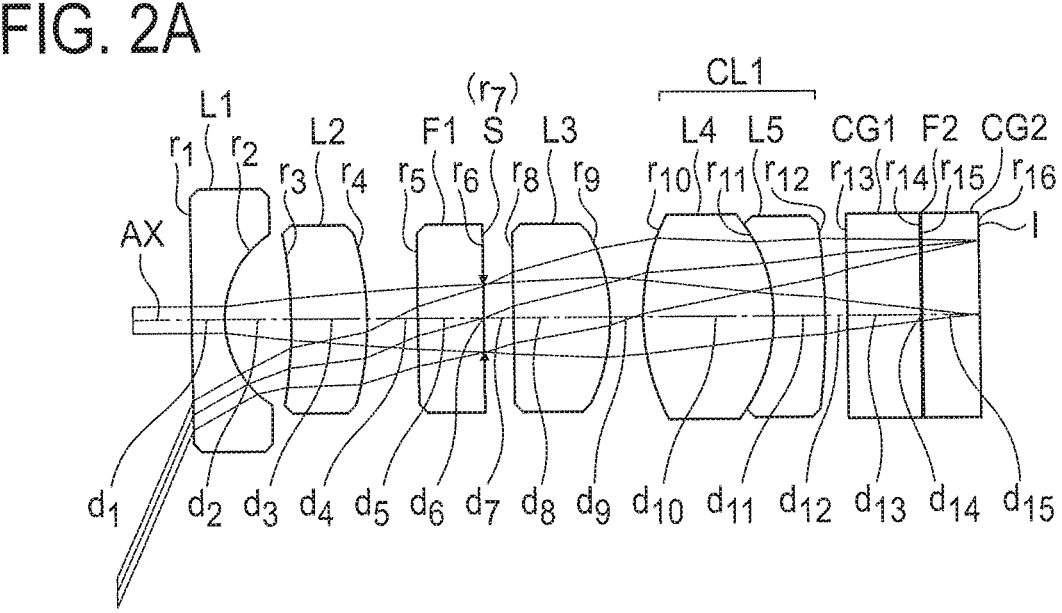
FIG. 2A is a diagram showing a cross-sectional view of a lens arrangement of an objective optical system for endoscope according to an example 1 of the present invention.
Figures 2B, 2C, 2D, 2E:
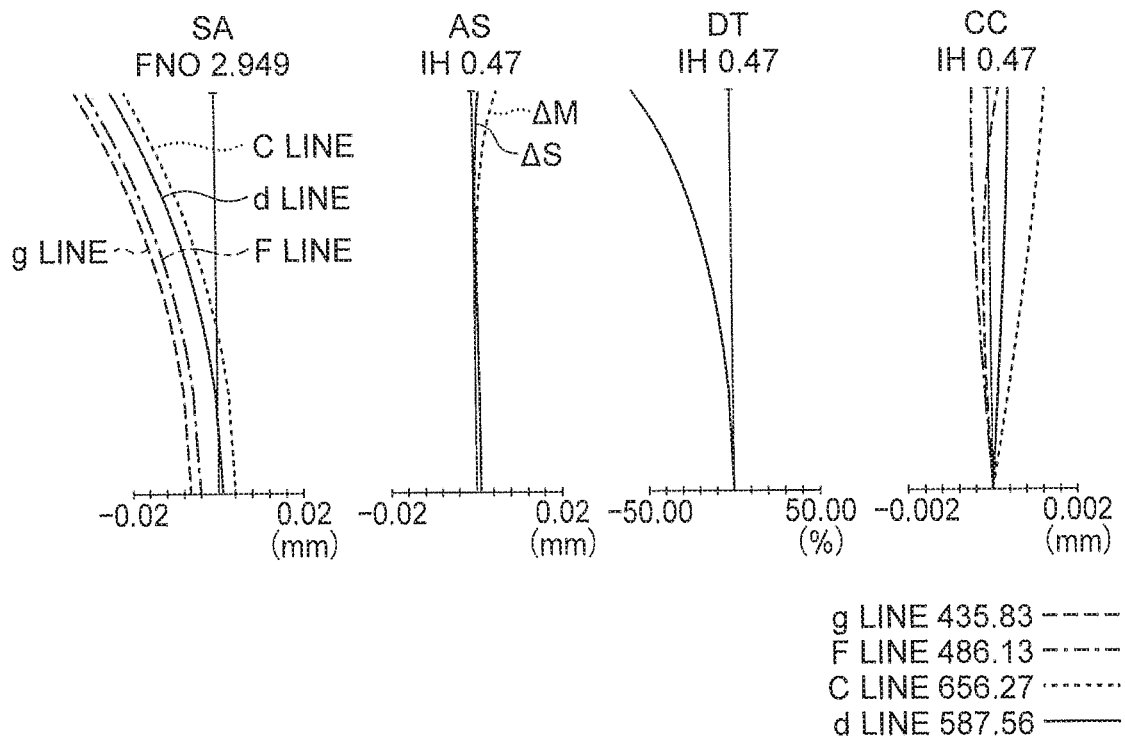
FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively, of the example 1.

An objective optical system for endoscope according to an example 1 will be described below. FIG. 2A is a diagram showing a cross-sectional view of a lens arrangement of the objective optical system for endoscope according to the present example.

The objective optical system for endoscope according to the present example includes in order from an object side, a first lens L1 which is a planoconcave negative lens having a flat surface directed toward the object side, a second meniscus lens L2 having a positive refractive power and having a convex surface directed toward an image side, an infrared absorbing filter F1, an aperture stop S, a third lens L3 which is a planoconvex positive lens having a flat surface directed toward the object side, a fourth lens L4 which is a biconvex positive lens, a fifth meniscus lens L5 having a negative refractive power and having a convex surface directed toward the image side, a cover glass CG1, and a CCD (charge coupled device) cover glass CG2. I is an image plane.

Moreover, a YAG (yttrium aluminum garnet) laser cut coating is applied to an object side of the infrared absorbing filter F1 and an LD laser cut coating is applied to an image side of the infrared absorbing filter F1.

Here, the fourth lens L4 having a positive refractive power and the fifth meniscus lens L5 having a negative refractive power are cemented. The cover glass CG1 and the CCD cover glass CG2 are cemented. Moreover, F2 is a cemented layer.

FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively, of the example 1.

Example 2

Figure 3A:
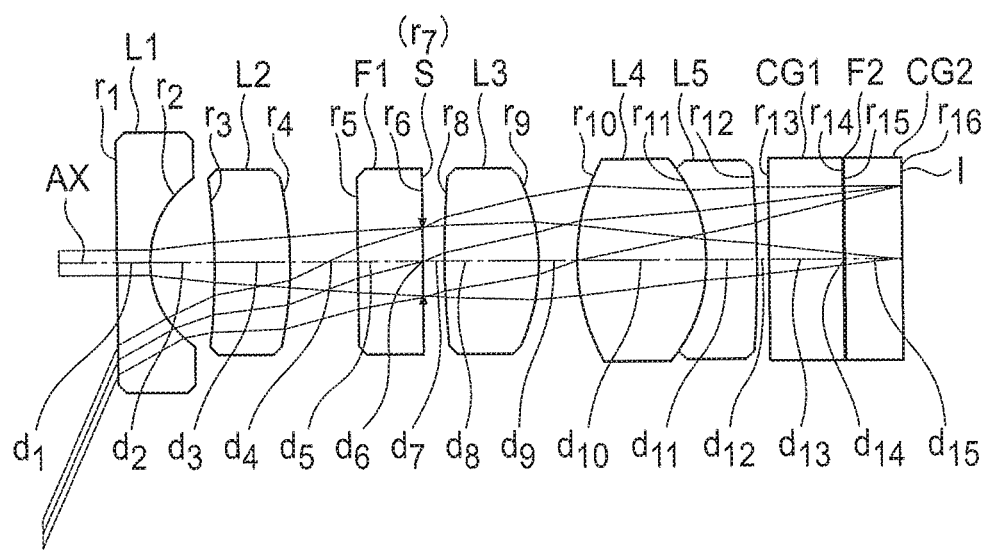
FIG. 3A is a diagram showing a cross-sectional view of a lens arrangement of an objective optical system for endoscope according to an example 2 of the present invention.
Figures 3B, 3C, 3D, 3E:
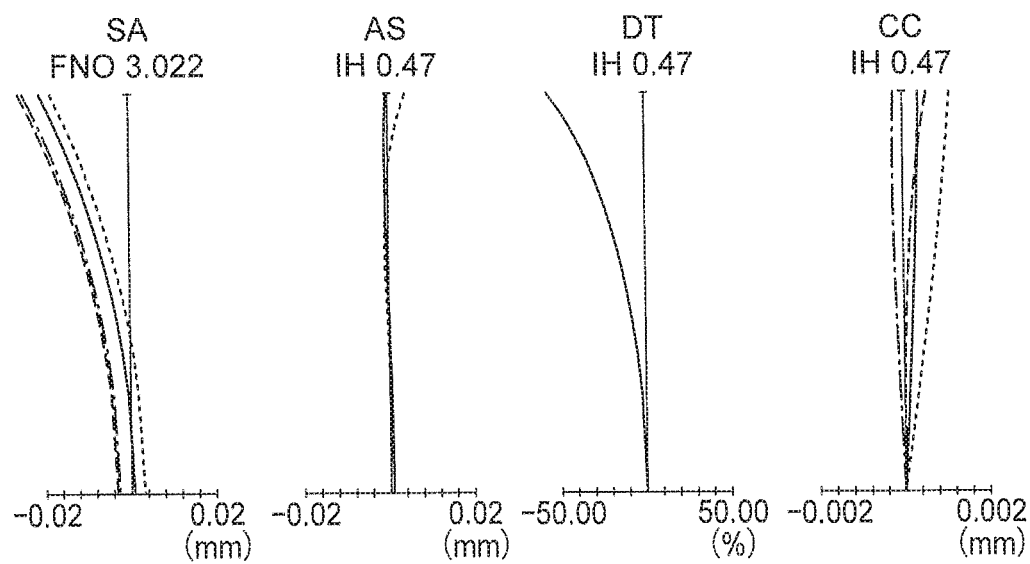
FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively, of the example 2.

An objective optical system for endoscope according to an example 2 will be described below. FIG. 3A is a diagram showing a cross-sectional view of a lens arrangement of the objective optical system for endoscope according to the present example.

The objective optical system for endoscope according to the present example includes in order from an object side, a first lens L1 which is a planoconcave negative lens having a flat surface directed toward the object side, a second meniscus lens L2 having a positive refractive power and having a convex surface directed toward an image side, an infrared absorbing filter F1, an aperture stop S, a third lens L3 which is a biconvex positive lens, a fourth lens L4 which is a biconvex positive lens, a fifth meniscus lens L5 having a negative refractive power and having a convex surface directed toward the image side, a cover glass CG1, and a CCD cover glass CG2. I is an image plane.

Moreover, a YAG laser cut coating is applied to an object side of the infrared absorbing filter F1 and an LD laser cut coating is applied to an image side of the infrared absorbing filter F1.

Here, the fourth lens L4 having a positive refractive power and the fifth meniscus lens L5 having a negative refractive power are cemented. The cover glass CG1 and the CCD cover glass CG2 are cemented. Moreover, F2 is a cemented layer.

FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively, of the example 2.

Example 3

Figure 4A:
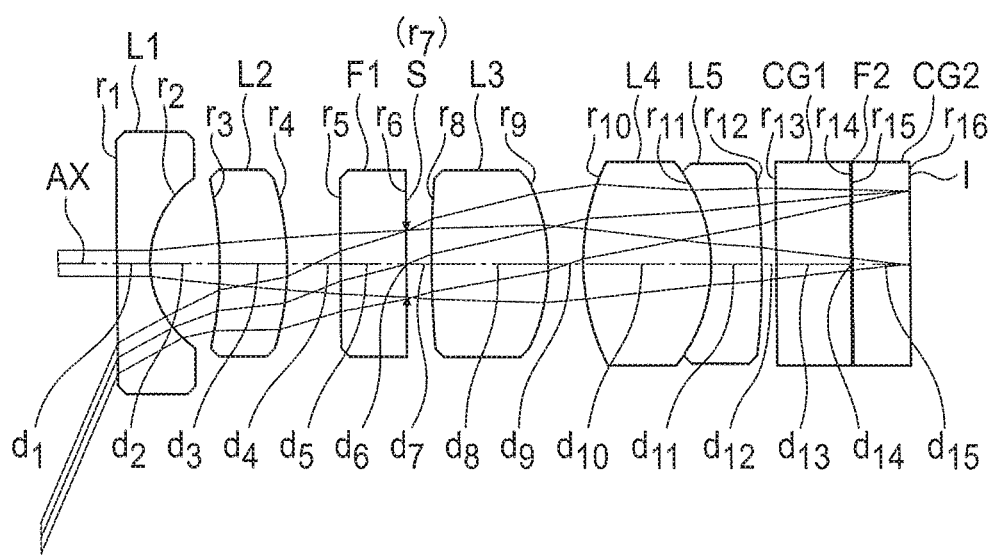
FIG. 4A is a diagram showing a cross-sectional view of a lens arrangement of an objective optical system for endoscope according to an example 3 of the present invention.
Figures 4B, 4C, 4D, 4E:
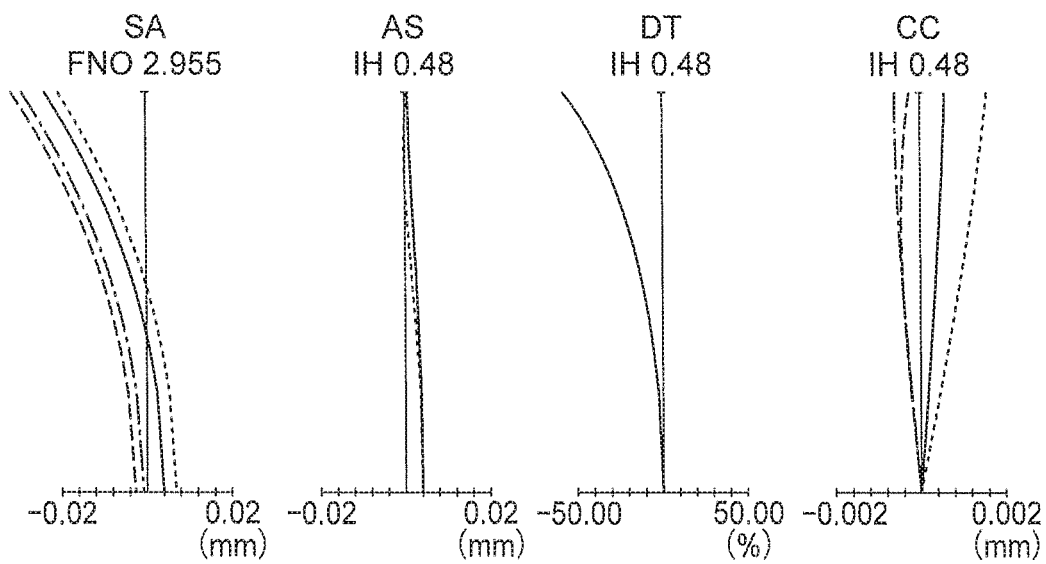
FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively, of the example 3.

An objective optical system for endoscope according to an example 3 will be described below. FIG. 4A is a diagram showing a cross-sectional view of a lens arrangement of the objective optical system for endoscope according to the present example.

The objective optical system for endoscope according to the present example includes in order from an object side, a first lens L1 which is a planoconcave negative lens having a flat surface directed toward the object side, a second meniscus lens L2 having a positive refractive power and having a convex surface directed toward an image side, an infrared absorbing filter F1, an aperture stop S, a third lens L3 which is a biconvex positive lens, a fourth lens L4 which is a biconvex positive lens, a fifth meniscus lens L5 having a negative refractive power and having a convex surface directed toward the image side, a cover glass CG1, and a CCD cover glass CG2. I is an image plane.

Moreover, a YAG laser cut coating is applied to an object side of the infrared absorbing filter F1 and an LD laser cut coating is applied to an image side of the infrared absorbing filter F1.

Here, the fourth lens L4 having a positive refractive power and the fifth meniscus lens L5 having a negative refractive power are cemented. The cover glass CG1 and the CCD cover glass CG2 are cemented. Moreover, F2 is a cemented layer.

FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively, of the example 3.

Numerical data of each example is shown below. Regarding symbols, r denotes a radius of curvature of each lens surface, d denotes a distance between two lenses, ne denotes a refractive index of each lens for an e-line, vd denotes Abbe's number for each lens, Fno denotes an F-number, and stop denotes an aperture stop.

Example 1

Unit mm

Surface data

| Surface no. | r | d | ne | vd |
|---|---|---|---|---|
| 1 | ∞ | 0.2115 | 1.88815 | 40.76 |
| 2 | 0.6603 | 0.4242 | | |
| 3 | −3.0889 | 0.4871 | 1.97189 | 17.47 |
| 4 | −1.9529 | 0.3281 | | |
| 5 | ∞ | 0.4230 | 1.49557 | 75.00 |
| 6 | ∞ | 0.0000 | | |
| 7(Stop) | ∞ | 0.1872 | | |
| 8 | ∞ | 0.6251 | 1.69979 | 55.53 |
| 9 | −1.1895 | 0.2131 | | |
| 10 | 1.4519 | 0.8357 | 1.65425 | 58.55 |
| 11 | −1.0589 | 0.3277 | 1.97189 | 17.47 |
| 12 | −4.3264 | 0.1405 | | |
| 13 | ∞ | 0.4759 | 1.51825 | 64.14 |
| 14 | ∞ | 0.0100 | 1.51500 | 64.00 |
| 15 | ∞ | 0.3700 | 1.50700 | 63.26 |
| 16 | ∞ | 0.0000 | | |
| Image pickup surface | ∞ | | | |

| Fno | 2.95 |
|---|---|
| Half angle of view | 66.2° |
| Image height | 0.475 mm |

Example 2

Unit mm

Surface data

| Surface no. | r | d | ne | vd |
|---|---|---|---|---|
| 1 | ∞ | 0.2094 | 1.88815 | 40.76 |
| 2 | 0.6637 | 0.4128 | | |
| 3 | −4.2118 | 0.4806 | 1.97189 | 17.47 |
| 4 | −2.5093 | 0.4327 | | |
| 5 | ∞ | 0.4188 | 1.49557 | 75.00 |
| 6 | ∞ | 0.0000 | | |
| 7(Stop) | ∞ | 0.1421 | | |
| 8 | 6.0661 | 0.6083 | 1.69979 | 55.53 |
| 9 | −1.2925 | 0.2488 | | |
| 10 | 1.3596 | 0.8311 | 1.65425 | 58.55 |
| 11 | −1.0170 | 0.3243 | 1.97189 | 17.47 |
| 12 | −7.1147 | 0.0792 | | |
| 13 | ∞ | 0.4711 | 1.51825 | 64.14 |
| 14 | ∞ | 0.0100 | 1.51500 | 64.00 |
| 15 | ∞ | 0.3700 | 1.50700 | 63.26 |
| 16 | ∞ | 0.0000 | | |
| Image pickup surface | ∞ | | | |

| Fno | 3.03 |
|---|---|
| Half angle of view | 65.9° |
| Image height | 0.47 mm |

Example 3

Unit mm

Surface data

| Surface no. | r | d | ne | vd |
|---|---|---|---|---|
| 1 | ∞ | 0.2123 | 1.88815 | 40.76 |
| 2 | 0.6781 | 0.4428 | | |
| 3 | −2.5569 | 0.4268 | 1.97189 | 17.47 |
| 4 | −1.8848 | 0.3455 | | |
| 5 | ∞ | 0.4245 | 1.49557 | 75.00 |
| 6 | ∞ | 0.0000 | | |
| 7(Stop) | ∞ | 0.1601 | | |
| 8 | 6.8568 | 0.7548 | 1.69979 | 55.53 |
| 9 | −1.2464 | 0.2227 | | |
| 10 | 1.5085 | 0.8224 | 1.65425 | 58.55 |
| 11 | −1.0645 | 0.3251 | 1.97189 | 17.47 |
| 12 | −5.2432 | 0.0933 | | |
| 13 | ∞ | 0.4776 | 1.51825 | 64.14 |
| 14 | ∞ | 0.0100 | 1.51500 | 64.00 |
| 15 | ∞ | 0.3700 | 1.50700 | 63.26 |
| 16 | ∞ | 0.0000 | | |
| Image pickup surface | ∞ | | | |

| Fno | 2.96 |
|---|---|
| Hail angle of view | 66.5° |
| Image height | 0.477 mm |

Corresponding values of the conditional expression are shown below.
Conditional Expression $$f1/f45 \tag{1-1}$$

$$(r3f+r3r)/(r3f-r3r) \tag{1-2}$$

$$d34/d4 \tag{1-3}$$

$$r4r/r3r \tag{2}$$

| | |
|---|---|
| $r4f/r5r$ | (3) |
| $r4f/r3f$ | (4) |
| $Ih/f3$ | (5) |
| $d1s/dsi$ | (6) |
| $f23/f$ | (7-1) |
| $r1r/r2f$ | (7-2) |
| $f3/f45$ | (8-1) |
| $f4/f5$ | (8-2) |
| $f2/r4r$ | (9-1) |
| $(r2f+r2r)/(r2f-r2r)$ | (9-2) |

Conditional Expression

| | Example1 | Example2 | Example3 |
|---|---|---|---|
| (1-1) | −0.29 | −0.26 | −0.26 |
| (1-2) | 1.00 | 0.65 | 0.69 |
| (1-3) | 0.25 | 0.30 | 0.27 |
| (2) | 0.89 | 0.79 | 0.85 |
| (3) | −0.34 | −0.19 | −0.29 |
| (4) | 0.00 | 0.22 | 0.22 |
| (5) | 0.28 | 0.30 | 0.30 |
| (6) | 0.59 | 0.63 | 0.57 |
| (7-1) | 2.84 | 2.79 | 2.72 |
| (7-2) | −0.21 | −0.16 | −0.27 |
| (8-1) | 0.65 | 0.54 | 0.53 |
| (8-2) | −0.71 | −0.82 | −0.76 |
| (9-1) | −4.26 | −5.51 | −5.28 |
| (9-2) | 4.44 | 3.95 | 6.61 |

The objective optical system for endoscope described above may satisfy the plurality of arrangements simultaneously. This is preferable for achieving a favorable objective optical system for endoscope. Moreover, combinations of the preferable arrangements are arbitrary. Furthermore, regarding each conditional expression, only an upper limit value or a lower limit value of a further restricted numerical range of conditional expression may be restricted.

Various embodiments of the present invention have been described heretofore. However, the present invention is not restricted to the embodiments described above and embodiments in which the arrangements of the embodiments described above are combined without departing from the scope of the invention are also in the category of the present invention.

As described heretofore, the present invention is useful for an objective optical system for endoscope having a fast Fno, a small size, and a high performance, which is strong against a manufacturing error.

The present invention shows an effect that it is possible to provide an objective optical system for endoscope having a fast Fno, a small size, and a high performance, which is strong against a manufacturing error.

What is claimed is:

1. An objective optical system for an endoscope, the objective optical system consisting of, in order from an object side:
   a first lens having a negative refractive power;
   a second meniscus lens having a positive refractive power and having a convex surface directed toward an image side;
   an aperture stop;
   a third lens having a positive refractive power; and
   a cemented lens of a fourth lens having a positive refractive power and a fifth lens having a negative refractive power,
   wherein the objective optical system satisfies the following conditional expressions (1-1), (1-2), and (1-3)

$$-0.6 \leq f1/f45 \leq -0.18 \quad (1\text{-}1)$$

$$0.2 \leq (r3f+r3r)/(r3f-r3r) \leq 1 \quad (1\text{-}2)$$

$$0.15 \leq d34/d4 \leq 0.7 \quad (1\text{-}3)$$

where,
f1 denotes a focal length of the first lens,
f45 denotes a combined focal length of the fourth lens and the fifth lens,
r3f denotes a radius of curvature of an object side of the third lens,
r3r denotes a radius of curvature of an image side of the third lens,
d34 denotes a distance along an optical axis between the third lens and the fourth lens, and
d4 denotes a thickness of the fourth lens.

2. The objective optical system according to claim 1, wherein the objective optical system satisfies the following conditional expression (2)

$$0.7 \leq r4r/r3r \leq 1.2 \quad (2)$$

where,
r4r denotes a radius of curvature of an image side of the fourth lens.

3. The objective optical system according to claim 1, wherein the objective optical system satisfies the following conditional expression (3)

$$-0.5 \leq r4f/r5r \leq -0.05 \quad (3)$$

where,
r4f denotes a radius of curvature of an object side of the fourth lens, and
r5r denotes a radius of curvature of an image side of the fifth lens.

4. The objective optical system according to claim 1, wherein the objective optical system satisfies the following conditional expression (4)

$$0 \leq r4f/r3f \leq 0.25 \quad (4)$$

where,
r4f denotes a radius of curvature of an object side of the fourth lens.

5. The objective optical system according to claim 1, wherein the objective optical system satisfies the following conditional expression (5)

$$0.24 \leq lh/f3 \leq 0.35 \quad (5)$$

where,
lh denotes a maximum image height of the objective optical system, and
f3 denotes a focal length of the third lens.

6. The objective optical system according to claim 1, wherein:
an image side of the aperture stop consists of, in order from the object side, the third lens and the cemented lens, and
the objective optical system satisfies the following conditional expression (6)

$$0.5 \leq d1s/dsi \leq 0.8 \quad (6)$$

where,
d1s denotes a distance along the optical axis from the first lens up to the aperture stop, and
dsi denotes a distance along the optical axis from the aperture stop up to an image plane.

7. The objective optical system according to claim 1, wherein the objective optical system satisfies the following conditional expressions (7-1) and (7-2)

$$2.3 \leq f23/f \leq 4 \quad (7\text{-}1)$$

$$-0.4 \leq r1r/r2f \leq -0.1 \quad (7\text{-}2)$$

where,
f23 denotes a combined focal length of the second meniscus lens and the third lens,
f denotes a focal length of the overall objective optical system,
r1r denotes a radius of curvature of an image side of the first lens, and
r2f denotes a radius of curvature of an object side of the second meniscus lens.

8. The objective optical system according to claim 1, wherein the objective optical system satisfies the following conditional expressions (8-1) and (8-2)

$$0.32 \leq f3/f45 \leq 1 \quad (8\text{-}1)$$

$$-1 \leq f4/f5 \leq -0.66 \quad (8\text{-}2)$$

where,
f3 denotes a focal length of the third lens,
f4 denotes a focal length of the fourth lens, and
f5 denotes a focal length of the fifth lens.

9. The objective optical system according to claim 1, wherein the objective optical system satisfies the following conditional expressions (9-1) and (9-2)

$$-6.5 \leq f2/r4r \leq -3.3 \quad (9\text{-}1)$$

$$3 \leq (r2f+r2r)/(r2f-r2r) \leq 10 \quad (9\text{-}2)$$

where,
f2 denotes a focal length of the second meniscus lens,
r4r denotes a radius of curvature of an image side of the fourth lens,
r2f denotes a radius of curvature of an object side of the second meniscus lens, and
r2r denotes a radius of curvature of an image side of the second meniscus lens.

10. The objective optical system according to claim 1, wherein focus adjustment at a time of assembling is carried out by changing a distance between the third lens and the fourth lens.

* * * * *